(12) United States Patent
Morimoto et al.

(10) Patent No.: US 8,053,500 B2
(45) Date of Patent: Nov. 8, 2011

(54) FLAME-RETARDANT POLYAMIDE RESIN COMPOSITION AND MOLDED ARTICLE

(75) Inventors: Kei Morimoto, Kanagawa (JP); Yasushi Yamanaka, Kanagawa (JP)

(73) Assignee: Mitsubishi Engineering-Plastics Corporation, Tokyo (JP)

( * ) Notice: Subject to any disclaimer, the term of this patent is extended or adjusted under 35 U.S.C. 154(b) by 0 days.

(21) Appl. No.: 12/517,493

(22) PCT Filed: Dec. 4, 2007

(86) PCT No.: PCT/JP2007/001341
§ 371 (c)(1),
(2), (4) Date: Oct. 15, 2009

(87) PCT Pub. No.: WO2008/068898
PCT Pub. Date: Jun. 12, 2008

(65) Prior Publication Data
US 2010/0069539 A1 Mar. 18, 2010

(30) Foreign Application Priority Data

Dec. 4, 2006 (JP) ................................. 2006-326530

(51) Int. Cl.
C08K 5/3492 (2006.01)
C08K 5/49 (2006.01)
C08K 5/5313 (2006.01)
C08K 5/04 (2006.01)
C08K 5/09 (2006.01)
C08K 7/02 (2006.01)
C08K 3/38 (2006.01)

(52) U.S. Cl. ......... 524/100; 524/115; 524/133; 524/494
(58) Field of Classification Search .................. 524/100, 524/115, 133, 494
See application file for complete search history.

(56) References Cited

U.S. PATENT DOCUMENTS

| | | | | |
|---|---|---|---|---|
| 6,031,032 A | * | 2/2000 | Horacek et al. | 524/100 |
| 7,358,285 B2 | * | 4/2008 | Ottenheijm | 524/100 |
| 2009/0159034 A1 | * | 6/2009 | Katayama et al. | 123/184.21 |
| 2010/0076137 A1 | | 3/2010 | Ogasawara et al. | |

FOREIGN PATENT DOCUMENTS

| | | |
|---|---|---|
| CN | 1163629 A | 10/1997 |
| EP | 0 246 620 A2 | 11/1987 |
| EP | 0 376 616 A2 | 7/1990 |
| EP | 0 400 935 A2 | 12/1990 |
| EP | 0 881 264 A2 | 12/1998 |
| EP | 0 994 156 A1 | 4/2000 |
| JP | 54-16565 | 2/1979 |
| JP | 62-268612 A | 11/1987 |
| JP | 2-173047 A | 7/1990 |
| JP | 7-18186 A | 1/1995 |
| JP | 7-21105 B2 | 3/1995 |
| JP | 7-133132 A | 5/1995 |
| JP | 7-291649 A | 11/1995 |
| JP | 10-219026 A | 8/1998 |
| JP | 11-43602 A | 2/1999 |
| JP | 2000-119514 A | 4/2000 |
| JP | 2000-119515 A | 4/2000 |
| JP | 2000-344541 A | 12/2000 |
| JP | 2001-72978 A | 3/2001 |
| JP | 2001-131409 A | 5/2001 |
| JP | 2002-53751 A | 2/2002 |
| JP | 2003-82228 A | 3/2003 |
| JP | 2003-201398 A | 7/2003 |
| JP | 2003-268231 A | 9/2003 |
| JP | 2004-292755 A | 10/2004 |
| JP | 2004-300189 A | 10/2004 |
| JP | 2005-307180 A | 11/2005 |
| JP | 2006-45390 A | 2/2006 |
| JP | 2007-70468 A | 3/2007 |
| WO | WO-96/09344 A1 | 3/1996 |
| WO | WO-2007/080754 A1 | 7/2007 |
| WO | WO 2008/062755 A1 | 5/2008 |

OTHER PUBLICATIONS

Hoshi F et al., "Reinforced thermoplastic resin compsn. with high flexural strength, etc.—is reinforced with powder of glass fibre with flat cross-sectional shape, used for moulding.", Jan. 20, 1995, XP-002471131.
Ito H, "Flat glass fiber-containing pellet for flat glass fiber-containing thermoplastic resin molded product, contains multiple flat glass fiber filaments with flat cross section, in pellet which contains thermoplastic resin", Feb. 16, 2006, XP-002471132.
Office Action dated Jul. 20, 2010 issued from Japanese Patent Office for the corresponding Japanese Patent Application No. 2007-312263.
Chinese Office Action dated Mar. 23, 2011 for corresponding Chinese Patent Application No. 31103155.
Office Action dated Apr. 11, 2011 for corresponding Japanese Patent Application No. 2007-312263. Office Action dated Oct. 27, 2010 for corresponding Japanese Patent Application No. 2007-312263.
Office Action dated Aug. 10, 2011 for corresponding Chinese Application No. 200780044696.6.
Office Action dated Aug. 16, 2011 for corresponding Japanese Application No. 2007-312263.

* cited by examiner

*Primary Examiner* — Kriellion A Sanders
(74) *Attorney, Agent, or Firm* — Birch, Stewart, Kolasch & Birch, LLP

(57) ABSTRACT

To provide a flame-retardant polyamide resin composition generally excellent in flame resistance, mechanical characteristics and electrical characteristics, and suitable for electrics/electronics components and vehicles. Used is a flame-retardant polyamide resin composition comprising, a polyamide resin (A), a phosphorus-containing flame retarder (B), and glass fiber having a non-circular cross-section (C), wherein the contents in the composition are 15 to 78% by weight for the polyamide resin (A), 2 to 20% by weight for the phosphorus-containing flame retarder (B), and 20 to 65% by weight for the glass fiber having a non-circular cross-section (C).

20 Claims, No Drawings

FLAME-RETARDANT POLYAMIDE RESIN COMPOSITION AND MOLDED ARTICLE

TECHNICAL FIELD

The present invention relates to a glass-fiber-reinforced, flame-retardant polyamide resin composition, and a molded article composed of the glass-fiber-reinforced, flame-retardant polyamide resin composition. The present invention relates particularly to a flame-retardant polyamide resin composition suitable for various components in the electrics/electronics industry including connector, breaker and magnet switch; and for materials for electrical components in the automotive industry. The present invention relates still particularly to a glass-fiber-reinforced, flame-retardant polyamide resin composition generally excellent in flame resistance, mechanical characteristics and electrical characteristics even added with a high concentration of glass fiber, unlikely to produce a highly-corrosive hydrogen halide gas, and excellent in moldability.

BACKGROUND ART

Polyamide resins have conventionally been used in industrial fields of automotive components, mechanical components, electrics/electronics components, by virtue of their excellent mechanical strength and heat resistance. In particular for applications to electrics/electronics components, required level of flame resistance has been elevated, even escalated up to a level of flame resistance higher than the self-extinction performance inherent to the polyamide resins. For this reason, investigations have extensively been made on elevation of flame resistance level, and more specifically on materials satisfying the level V-0 specified by UL94 by Underwriters Laboratories. In particular, as for compositions mixed with a high concentration of glass fiber, there have been growing demands on development using a non-halogen-type flame retarder, following the trend of time. In these applications, also demands on the tracking resistance, represented by IEC Standards in Europe, have been becoming more and more stringent.

Patent Document 1 discloses a polyamide resin composition composed of melamine cyanurate and/or its derivative, and an inorganic filler, excellent in mechanical characteristics, thermal characteristics and flame resistance. The level of flame resistance is, however, V-2 specified by UL 94, while giving no disclosure on resin compositions having flame resistance of higher levels, more specifically, the level V-1 or higher.

Patent Document 2 is an invention which relates to a flame retarder combination containing a component, as a first component, which contains phosphinate salt represented by a specific structure and/or a diphosphinate salt represented by a specific structure and/or a polymer of these species; and a second component which contains a condensed product of melamine and/or a reaction product of melamine with phosphoric acid and/or a reaction product of a condensed product of melamine with phosphoric acid and/or a mixture of these species. The Patent Document 2 describes also a method of using the flame retarder combination for the purpose of turning thermoplastic resins into flame retardant resins. In Example, there is exemplified a polyamide resin composition satisfying flame resistance of the level V-0 specified by UL94 (1/16 inches thick), obtained by mixing a reinforced polyamide resin containing 30% of glass fiber, with a flame retarder combination composed of a phosphinate salt (first component) and melamine polyphosphate (second component).

The polyamide resin composition exemplified in Example is, however, discussed only for its data on flame resistance, while giving no description on any other characteristics including mechanical characteristics and electrical characteristics.

Patent Document 3 discloses a flame-retardant polyamide resin composition containing the flame retarder combination (containing 1 to 30% by weight of each of the first component and the second component) disclosed in Patent Document 2; and 5 to 40% by weight of an inorganic filler (glass fiber, wollastonite, talc, calcined kaolin, mica, etc.). In Examples, there is described that polyamide resin compositions containing 20% by weight and 30% by weight of glass fiber exhibit excellent flame resistance and tracking resistance. The resin composition may, however, be degraded in the mechanical strength by mixing of the flame retarder. No description is given on the sectional geometry of the glass fiber.

Patent Document 4 discloses a flame-retardant aromatic polyamide resin composition obtained by mixing (a) 100 parts by weight of aromatic polyamide resin, (b) 0.1 to 100 parts by weight of crosslinked phosphazene compound, (c) 1 to 60 parts by weight of inorganic fibrous material, and (d) 1 to 60 parts by weight of magnesium hydroxide. Claim 1 of Patent Document 4 specifies the amount of mixing of the (c) inorganic fibrous material as 1 to 60 parts by weight relative to 100 parts by weight of the (a) aromatic polyamide resin, but the amount of mixing of the (c) component described in Example is only as much as 7 parts by weight or around, showing no specific examples relevant to mixing at high concentrations.

There is no description also on exemplary cases of using a glass fiber as the (c) component. Example shows data on the flame resistance, but shows no data on the mechanical strength. The resin composition manufactured by adopting the technique disclosed in Patent Document 4 may sometimes be degraded in the mechanical strength, providing difficulty in reconciling flame resistance and mechanical strength even if the technique is adopted.

Patent Document 5 describes that, by using the glass fiber having a flattened cross-sectional geometry, instead of glass fiber which is a representative reinforcing fiber, the glass fiber is increased in the specific surface area from the cross-sectioned glass fiber having the circular, thereby the adhesive effect with a matrix resin composition increases, and describes also that the mechanical strength may be improved, by elongating the length of fiber in a molded article (average fiber length is 0.57 mm for a cocoon-like sectional geometry, in contrast to 0.47 mm for a circular sectional geometry). Patent Document 5, however, exemplifies only the cases applied to PBT resin, AS resin and ABS resin. These resin compositions might be effective in improvement in the tensile strength and surface smoothness, and in prevention of warping as compared with a circular cross-sectioned glass fiber, but the impact strength thereof is almost equivalent to the impact strength of a resin composition using a circular cross-sectioned glass fiber particularly when a polyamide resin is used as the thermoplastic resin, and the impact strength thereof is insufficient for practical molded articles use. There is no description on specific examples of mixing of a flame retarder, nor description on correlation of the cross-sectional geometry of glass fiber and the flame resistance.

Patent Document 6 discloses a flame-retardant polyester resin composition composed of (A) a crystalline thermoplastic polyester resin, (B) 1 to 60% by weight (in composition) of glass fiber having a flattened sectional geometry characterized by a ratio of the major axis of a section perpendicular to the longitudinal direction (longest straight distance of the section) to the minor axis (longest straight distance in the direction perpendicular to the major axis) of 1.5 to 5, (C) 0.5 to 25% by weight (in composition) of a halogen-containing organic flame retarder, and (D) 0.1 to 20% by weight (in composition) of an inorganic flame retardant additive. The technique, however, adopts the (C) halogen-containing organic flame retarder, wherein addition of the flame retarder may be causative of degradation in the mechanical strength such as impact resistance, or production of a hydrogen halide gas in the process of combustion, raising problems of pollution of mold, and failure in obtaining a molded article of good appearance. Moreover, Patent Document 6 gives no description still also on correlation between the sectional geometry of glass fiber and flame resistance.

Patent Document 1: Japanese Laid-Open Patent Publication No. S54-16565
Patent Document 2: Japanese Laid-Open Patent Publication No. 2001-72978
Patent Document 3: Japanese Laid-Open Patent Publication No. 2004-292755
Patent Document 4: Japanese Laid-Open Patent Publication No. 2001-131409
Patent Document 5: Japanese Laid-Open Patent Publication No. S62-268612
Patent Document 6: Japanese Examined Patent Publication No. H7-21105

DISCLOSURE OF THE INVENTION

Subjects to be Solved by the Invention

The present invention is conceived after considering the above-described situation, and an object of the present invention is to provide a flame-retardant polyamide resin composition generally excellent in flame resistance, mechanical characteristics and electrical characteristics, unlikely to produce a highly-corrosive hydrogen halide gas, and excellent in moldability, and a molded article composed of the polyamide resin composition.

Means for Solving Problems

Aiming at solving the above-described problems, the present inventors found out after our extensive investigations that a high level of flame resistance, such the level V-0 specified by UL94, may be achievable by adding a glass fiber having a non-circular cross-section, particularly when the glass fiber is added to a polyamide resin, and more particularly when added to as much as 20% by weight or more of the resin composition, but without inducing degradation in the mechanical strength by addition of the flame retarder.

According to the present invention, there is provided a flame-retardant polyamide resin composition containing (A) a polyamide resin, (B) a phosphorus-containing flame retarder, and (C) a glass fiber having a non-circular cross-section, wherein the contents in the composition are 15 to 78% by weight for the (A) polyamide resin, 2 to 20% by weight for the (B) phosphorus-containing flame retarder, and 20 to 65% by weight for the (C) glass fiber having a non-circular cross-section.

ADVANTAGE OF THE INVENTION

The polyamide resin composition of the present invention does not produce any highly-corrosive hydrogen halide gas in the process of combustion, and excellent in the mechanical characteristics and electrical characteristics even when the glass fiber is mixed, particularly even when a high concentration of glass fiber is mixed, so that the polyamide resin composition is suitable for various components in the electrics/electronics industry including connector, breaker and magnet switch; and for materials for electrical components in the industrial field of vehicles such as automobiles.

BEST MODES FOR CARRYING OUT THE INVENTION

The present invention will be detailed below.

The (A) polyamide resin used in the present invention is a polyamide polymer having acid amide groups (—CONH—) in the molecule thereof, and can be melted under heating. More specifically, it is any one of various polyamide resins such as polycondensation product of lactam, polycondensation product of diamine compound with dicarboxylic acid compound, and polycondensation product of ω-aminocarboxylic acid; or a copolymerized polyamide resin thereof or blends of thereof.

The lactam used as a source material for polycondensation of the polyamide resin may be exemplified by ε-caprolactam, ω-laurolactam and so forth.

The diamine compound may be exemplified by aliphatic, alicyclic and aromatic diamines including tetramethylene diamine, hexamethylene diamine, undecamethylene diamine, dodecamethylene diamine, 2-methyl pentamethylene diamine, (2,2,4- or 2,4,4-)trimethyl hexamethylene diamine, 5-methyl nonamethylene diamine, metaxylylene diamine (MXDA), paraxylylene diamine, 1,3-bis(aminomethyl)cyclohexane, 1,4-bis(aminomethyl)cyclohexane, 1-amino-3-aminomethyl-3,5,5-trimethyl cyclohexane, bis(4-aminocyclohexyl) methane, bis(3-methyl-4-aminocyclohexyl)methane, 2,2-bis(4-aminocyclohexyl) propane, bis (aminopropyl) piperazine, and aminoethyl piperazine.

The dicarboxylic acid compound may be exemplified by aliphatic, alicyclic and aromatic dicarboxylic acids including adipic acid, suberic acid, azelaic acid, sebacic acid, dodecanedioic acid, terephthalic acid, isophthalic acid, 2-chloroterephthalic acid, 2-methyl terephthalic acid, 5-methylisophthalic acid, sodium 5-sulfoisophthalate, hexahydroterephthalic acid, and hexahydroisophthalic acid.

The ω-aminocarboxylic acid may be exemplified by amino acids including 6-aminocaproic acid, 11-aminoundecanoic acid, 12-aminododecanoic acid, and paraminomethyl benzoate.

Specific examples of the polyamide resin obtained by polycondensation of these source materials include polyamide 4, polyamide 6, polyamide 11, polyamide 12, polyamide 46, polyamide 66, polyamide 610, polyamide 612, polyhexamethylene terephthalamide (polyamide 6T), polyhexamethylene isophthalamide (polyamide 6I), polymetaxylylene adipamide (polyamide MXD6), polymetaxylylene dodecamide, polyamide 9T, and polyamide 9MT. In the present invention, these polyamide homopolymers or copolymers may be used independently, or in a form of mixture.

Among the above-described polyamide resins, those more preferably adoptable from the viewpoints of moldability and heat resistance include polyamide 6, polyamide 66, or a xylylene diamine-base polyamide resin (MX nylon) obtained by polycondensation of α,ω-straight-chain aliphatic dibasic acid and xylylene diamine. Among these, MX nylon is more preferable from the viewpoints of heat resistance and flame resistance. For the case where the (a) polyamide resin is a mixture, the ratio of MX nylon in the (a) polyamide resin is preferably 50% by weight or above, and more preferably 80% by weight or above.

MX nylon is slightly lower in the crystallization speed as compared with aliphatic polyamide resins such as polyamide 66, polyamide 6, polyamide 46, and polyamide 9T. When MX nylon is adopted, it is therefore preferable to use MX nylon while being mixed with an aliphatic polyamide resin, in order to shorten the molding cycle.

The aliphatic polyamide resin used for the above-described purpose of shortening the molding cycle may be exemplified by slowly-crystallizable polyamide resins such as polyamide 66, polyamide 6, polyamide 46, and polyamide 9T; and high-melting-point polyamide resins such as polyamide 66/6T, and 66/6T/6I, wherein polyamide 66 or polyamide 6 is preferable from the viewpoint of economy. In view of balance between the moldability and physical characteristics, the content of the aliphatic polyamide resin may preferably be adjusted to less than 50% by weight of the total polyamide resin. By adjusting the content of the aliphatic polyamide resin to less than 50% by weight, the heat resistance may be kept at a desirable level.

Among the α,ω-straight-chain aliphatic dibasic acid used as a source material of MX nylon, those preferably used may be exemplified by α,ω-straight-chain aliphatic dibasic acids having 6 to 20 carbon atoms, such as adipic acid, sebacic acid, suberic acid, dodecanedioic acid, and eicosadioic acid. Among these α,ω-straight-chain aliphatic dibasic acids, adipic acid may be particularly preferable, taking balance between moldability and performances of the molded article into consideration.

The xylylene diamine used as another source material for MX nylon may be metaxylylene diamine, or a mixed xylylene diamine composed of paraxylylene diamine and metaxylylene diamine. The molar ratio of metaxylylene diamine and paraxylylene diamine (metaxylylene diamine/paraxylylene diamine) in the mixed xylylene diamine is preferably adjusted to 55/45 to 100/0, and more preferably to 70/30 to 100/0. By adjusting the molar ratio of paraxylylene diamine to less than 45 mol %, the melting point of the polyamide resin may preferably be kept low, and polymerization of MX nylon, or molding of a composition containing MX nylon may preferably be facilitated. In particular, the ratio of paraxylylene diamine may further preferably be adjusted to 10 mol % or above, because the crystallization speed of the polyamide resin may be increased, and the content of the aliphatic polyamide resin may be reduced.

The number-average molecular weight of the polyamide resin is preferably in the range from 6,000 to 40,000, and more preferably from 10,000 to 20,000. The polyamide resin composition may be prevented from being embrittled, by adjusting the molecular weight to 6,000 or above, and may be improved in the fluidity in the process of molding, and thereby facilitated in molding, by adjusting the value to 40,000 or smaller.

The concentration of amino terminal of the polyamide resin is preferably 10 to 140 meq/kg, and more preferably 30 to 100 meq/kg from the viewpoint of molecular weight of polymer. On the other hand, the concentration of carboxyl terminal of the polyamide resin is preferably 10 to 140 meq/kg, and more preferably 30 to 100 meq/kg from the viewpoint of molecular weight of polymer.

The (B) phosphorus-containing flame retarder used in the present invention is a flame retarder containing a phosphorus atom, and may be exemplified by (a) reaction products of melamine with phosphoric acid, (b) (di)phosphinate salts, and (c) phosphazene compounds. Each flame retarder may be used independently, or two or more species thereof may be used in combination.

The (a) reaction products of melamine with phosphoric acid means those obtained by a substantially equimolar reaction of melamine or condensed product of melamine, with phosphoric acid, pyrophosphoric acid or polyphosphoric acid, and the manufacturing methods are not limited. In general, melamine polyphosphate (chemical formula "$(C_3H_6N_6 \cdot HPO_3)_n$", where n represents degree of condensation) obtained by condensing melamine phosphate by heating under a nitrogen atmosphere, may be exemplified.

The phosphoric acid composing the melamine phosphate may be exemplified specifically by orthophosphoric acid, phosphorous acid, hypophosphorous acid, metaphosphoric acid, pyrophosphoric acid, triphosphoric acid, and tetraphosphoric acid. In particular, melamine polyphosphate obtained by condensing an adduct of orthophosphoric acid or pyrophosphoric acid with melamine is preferable by virtue of its large effect as a flame retardant. From the viewpoint in particular of heat resistance, the degree of condensation n of the melamine polyphosphate is preferably 5 or larger.

The melamine polyphosphate may alternatively be an equimolar addition salt of polyphosphoric acid with melamine, but not limited to those in which all of the polyphosphoric acid and melamine form the addition salt, while allowing mixtures of these species. In other words, as the polyphosphoric acid forming the addition salt with melamine, so-called condensed phosphoric acid such as chainlike polyphosphoric acid and cyclic polymetaphosphoric acid may be adoptable. The degree of condensation n of these polyphosphoric acids is generally 3 to 50, but not specifically limited, where the degree of condensation n of the polyphosphoric acid used herein is preferably 5 or larger, in view of heat resistance of the resultant addition salt of the melamine polyphosphate. The addition salt of the melamine polyphosphate is a powder obtained by preparing an aqueous slurry of a mixture of melamine with polyphosphoric acid; thoroughly mixing the slurry so as to produce a reaction product of the both in a form of fine particle; filtering the slurry; washing, drying and optionally sintering the product; and crushing thus obtained solid matter.

Alternatively, the melamine polyphosphate may be an addition salt of phosphoric acid with a melamine condensed product, but not limited to those in which all of phosphoric acid and the melamine condensed product form the addition salt, while allowing mixtures of these species. The melamine condensed product capable of forming the addition salt together with phosphoric acid may be exemplified by melem, melam, and melon.

In the present invention, taking the mechanical strength and appearance of the molded article into consideration, it may be preferable to use melamine polyphosphate powder crushed so as to adjust the weight-average particle size preferably to 100 μm or smaller, and more preferably to 50 μm or smaller. In particular, use of powder as fine as 0.5 to 20 μm may be preferable, not only because a high level of flame resistance may be exhibited, but also because the molded article may distinctively be improved in the strength. It is not always necessary for the melamine polyphosphate to be completely pure, allowing slight residues of unreacted melamine, melamine condensed product, phosphoric acid, and polyphosphoric acid. The melamine polyphosphate having a phosphorus content of 8 to 18% by weight may be particularly preferable, in view of suppressing adhesion of pollutants to the molds in the process of molding.

The content of the (a) reaction product of melamine with phosphoric acid is preferably 2 to 12% by weight, and more preferably 3 to 10% by weight, of the composition of the present invention. It may be preferable to adjust the content of the (a) component to 2% by weight or more, in view of thoroughly improving the flame resistance, and it may be preferable to adjust the content to 12% by weight or less, in view of reducing the gas, and of suppressing any troubles in the process of extrusion or molding.

The (b) (di)phosphinate salt used in the present invention is a phosphinate salt represented by the formula (I) below and/or diphosphinate salt represented by the formula (II) below, and may be exemplified by those manufactured by using phosphinate together with metal carbonate, metal hydroxide or metal oxide, in an aqueous medium. The (di)phosphinate salt is intrinsically a monomeric compound, but may be given as a polymeric phosphinate salt having a degree of condensation of 1 to 3, depending on environments, while being affected by reaction conditions.

[Chemical Formula 1]

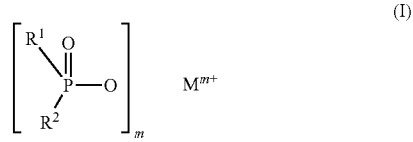

(I)

[Chemical Formula 2]

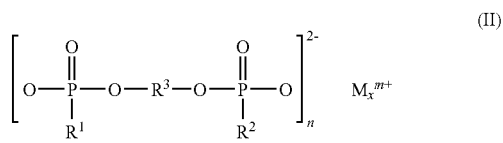

(II)

(in the formulae (I) and (II), each of $R^1$ and $R^2$ represents a linear or branched alkyl group having 1 to 6 carbon atoms (denoted as "$C_1$-$C_6$", hereinafter) and/or $C_6$-$C_{10}$ aryl group, $R^3$ represents a linear or branched $C_1$-$C_{10}$ alkylene group, $C_6$-$C_{10}$ arylene group, $C_7$-$C_{10}$ alkylarylene group, or $C_7$-$C_{10}$ aryl alkylene group, M represents Ca, Mg, Al and/or Zn, m represents M-valent, written as 2n=mx, n represents 1 or 3, and x represents 1 or 2.)

For the case where m or n is 2 or larger, each of $R^1$ to $R^3$ may be same with, or different from each other.

The phosphinic acid may be exemplified by dimethyl phosphinate, ethyl methyl phosphinate, diethyl phosphinate, methyl-n-propyl phosphinate, methane di(methyl phosphinate), benzene-1,4-di(methyl phosphinate), methyl phenyl phosphinate and diphenyl phosphinate. The metal component (M) may be exemplified by calcium ion, magnesium ion, aluminum ion and/or zinc ion.

The phosphinate salt may be exemplified by calcium dimethyl phosphinate, magnesium dimethyl phosphinate, aluminum dimethyl phosphinate, zinc dimethyl phosphinate, calcium ethyl methyl phosphinate, magnesium ethyl methyl phosphinate, aluminum ethyl methyl phosphinate, zinc ethyl methyl phosphinate, calcium diethyl phosphinate, magnesium diethyl phosphinate, aluminum diethyl phosphinate, zinc diethyl phosphinate, calcium methyl-n-propyl phosphinate, magnesium methyl-n-propyl phosphinate, aluminum methyl-n-propyl phosphinate, zinc methyl-n-propyl phosphinate, calcium methyl phenyl phosphinate, magnesium methyl phenyl phosphinate, aluminum methyl phenyl phosphinate, zinc methyl phenyl phosphinate, calcium diphenyl phosphinate, magnesium diphenyl phosphinate, aluminum diphenyl phosphinate, and zinc diphenyl phosphinate.

The diphosphinate salt may be exemplified by calcium methane di(methyl phosphinate), magnesium methane di(methyl phosphinate), aluminum methane di(methyl phosphinate), zinc methane di(methyl phosphinate), calcium benzene-1,4-di(methyl phosphinate), magnesium benzene-1,4-di(methyl phosphinate), aluminum benzene-1,4-di(methyl phosphinate), and zinc benzene-1,4-di(methyl phosphinate).

Among these (di)phosphinate salts, aluminum ethyl methyl phosphinate, aluminum diethyl phosphinate, and zinc diethyl phosphinate are particularly preferable, from the viewpoint of electrical characteristics.

In the present invention, taking the mechanical strength and appearance of the molded article into consideration, it may be preferable to use (di)phosphinate salt powder crushed so as to adjust the weight-average particle size preferably to 100 μm or smaller, and more preferably to 80 μm or smaller. In particular, use of powder as fine as 0.5 to 50 μm may be preferable, not only because a high level of flame resistance may be exhibited, but also because the molded article may distinctively be improved in the strength. In addition, the (di)phosphinate salt having a phosphorus atom content of 5 to 40% by weight may be particularly preferable, in view of suppressing adhesion of pollutants to the molds in the process of molding. The (di)phosphinate salt acts as a flame retarder, and may exhibit excellent flame resistance and excellent electrical characteristics, when used in combination with the (a) reaction product of melamine and phosphoric acid.

The content of the (b) (di)phosphinate salt is preferably 3 to 12% by weight, and more preferably 5 to 10% by weight of the composition of the present invention. The flame resistance may thoroughly be improved by adjusting the content of the (b) component to 3% by weight or more, and failure in mold releasing and mold deposit may preferably be suppressed and the molding may preferably be facilitated by adjusting the content to 12% by weight or less.

The (c) phosphazene compound used in the present invention is an organic compound having a —P=N— bond in the molecule, and is preferably at least one species of compound selected from the group consisting of cyclic phenoxyphosphazene represented by the formula (III) below; chainlike phenoxyphosphazene represented by the formula (IV) below; and crosslinked phenoxyphosphazene compound obtained by crosslinking at least one species of phenoxyphosphazene selected from those represented by the formulae (III) and (IV) below, with a crosslinking group represented by the formula (V) below. Since the (c) phosphazene compound has a strong effect of flame retardation, and can exhibit an excellent flame resistance even with a small content, in particular when combined with the metal borate described later, so that degradation in the mechanical strength and generation of gas, possibly induced by mixing of the flame retarder, may preferably and more readily be suppressed.

[Formula 3]

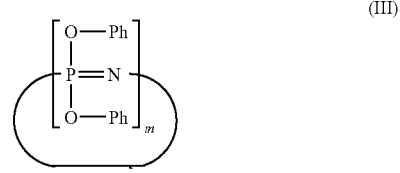

(III)

(in the formula (III), m represents an integer from 3 to 25, and Ph represents a phenyl group.)

[Formula 4]

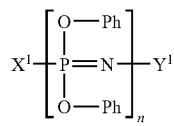
(IV)

(in the formula (IV), $X^1$ represents —N=P(OPh)$_3$ group or —N=P(O)OPh group, $Y^1$ represents —P(OPh) 4 group or —P(O) (OPh)$_2$ group, n represents an integer from 3 to 10000, and Ph represents a phenyl group.)

[Formula 5]

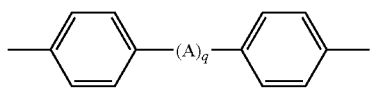
(V)

(in the formula (V), A represents —C(CH$_3$)$_2$—, —SO$_2$—, —S—, or —O—, and q is 0 or 1.)

The cyclic phenoxyphosphazene compound represented by the formula (III) may be exemplified by compounds such as phenoxy cyclotriphosphazene, octaphenoxy cyclotetraphosphazene, and decaphenoxy cyclopentaphosphazene, obtained by allowing ammonium chloride and phosphorus pentachloride to react at 120 to 130° C. to obtain a mixture containing cyclic and straight chain chlorophosphazenes, extracting cyclic chlorophosphazenes such as hexachloro cyclotriphosphazene, octachloro cyclotetraphosphazene, and decachloro cyclopentaphosphazene, and then substituting with phenoxy group. The cyclic phenoxyphosphazene compound may preferably be a compound in which m in the formula (III) represents an integer from 3 to 8.

The chainlike phenoxyphosphazene compound represented by the formula (IV) may be exemplified by a compound obtained by subjecting hexachloro cyclotriphosphazene, obtained by the above-described method, to ring-opening polymerization at 220 to 250° C., and then substituting thus obtained chainlike dichlorophosphazene having a degree of polymerization of 3 to 10000 with phenoxy groups. The chain-like phenoxyphosphazene compound preferably has a value of n in the formula (IV) of 3 to 1000, more preferably 3 to 100, and still more preferably 3 to 25.

The crosslinked phenoxyphosphazene compound may be exemplified by compounds having crosslinked structures of 4,4'-diphenylene group, such as a compound having a crosslinked structure of 4,4'-sulfonyldiphenylene (bisphenol S residue), a compound having a crosslinked structure of 2,2-(4,4'-diphenylene) isopropylidene group, a compound having a crosslinked structure of 4,4'-oxydiphenylene group, and a compound having a crosslinked structure of 4,4'-thiodiphenylene group. The phenylene group content of the crosslinked phenoxyphosphazene compound is generally 50 to 99.9%, and preferably 70 to 90%, based on the total number of phenyl group and phenylene group contained in the cyclic phosphazene compound represented by the formula (III) and/or the chainlike phenoxyphosphazene compound represented by the formula (IV). The crosslinked phenoxyphosphazene compound may be particularly preferable if it doesn't have any free hydroxyl groups in the molecule thereof.

The cyclic phenoxyphosphazene compound and the chain-like phenoxyphosphazene compound may be synthesized according to methods described, for example, in "Phosphorus-Nitrogen Compounds (Academic Press, (1972))", written by H. R. Allcook, and "Inorganic Polymers (Prentice-Hall International, Inc. (1992))", co-written by J. E. Mark, H. R. Allcook and R. West.

The content of the (c) phosphazene compound is preferably 1 to 8% by weight in the composition of the present invention, and more preferably 1.5 to 6% by weight. The flame resistance may thoroughly be improved by adjusting the content of the (b) component to 1% by weight or more, and the mechanical strength may be kept to a desirable level by adjusting the content to 8% by weight or less.

In the present invention, the (a) reaction product of melamine with phosphoric acid, and the (b) (di)phosphinate salt may preferably be used in combination as the (B) phosphorus-containing flame retarder. The total content of both components may preferably be 2 to 12% by weight, and more preferably 3 to 10% by weight, in the composition of the present invention. The ratio of contents of both components may preferably be (a)/(b)=40/60 to 60/40. By adjusting the ratio of contents by weight to the above-described ranges, the flame resistance and the tracking resistance may effectively be improved, and production of gas in the process of molding may preferably be reduced.

In the present invention, for the purpose of suppressing production of gas or mold deposit in the process of molding, and bleeding of the flame retarder, it may be preferable to add one species or more species of thermoplasitic resins described below, which is compatible with the (B) phosphorus-containing flame retarder.

The thermoplastic resin other than the polyamide resin may be exemplified by olefinic resins such as polypropylene (PP) and polyethylene (PE); styrene-base polymers; polyester-base resins such as poly(butylene terephthalate) (PBT) and poly(ethylene terephthalate) (PET); polycarbonate-base resins; poly(phenylene ether)-base resins; poly(methyl methacrylate) resin; poly(phenylene sulfone) resins; poly(tetrafluoroethylene) resins; novolac phenol resins; and liquid crystal resins. From the viewpoint of compatibility with the (B) phosphorus-containing flame retarder, in particular with the (c) phosphazene compound, preferable examples include styrene-base polymers, polycarbonate-base resins, and poly(phenylene ether)-base resin, wherein poly(phenylene ether)-base resins, or mixed resin of poly(phenylene ether)-base resin and styrene-base polymer.

The poly(phenylene ether)-base resins may be exemplified by poly(2,6-dimethyl-1,4-phenylene)ether, poly(2,6-diethyl-1,4-phenylene)ether, poly(2,6-dipropyl-1,4-phenylene)ether, poly(2-methyl-6-ethyl-1,4-phenylene)ether, and poly(2-methyl-6-propyl-1,4-phenylene)ether, wherein poly(2,6-dimethyl-1,4-phenylene)ether is particularly preferable.

The styrene-base polymers may be exemplified by styrene-base resins such as general-purpose polystyrene (GPPS), rubber-reinforced polystyrene (HIPS), acrylonitrile-styrene copolymer (AS resin), acrylonitrile-butadiene-styrene copolymer (ABS resin), and methyl methacrylate-butadiene-styrene copolymer (MBS resin); and styrene-base elastomers such as styrene-ethylene-butadiene-styrene copolymer (SEBS), and styrene-ethylene-propylene-styrene copolymer (SEPS), wherein styrene-base elastomers are preferable.

When the poly(phenylene ether)-base resin and the styrene-base polymer are used in combination, the content by weight of the both (poly(phenylene ether)-base resin/styrene-base resin) is preferably 99/1 to 20/80, and more preferably 97/3 to 40/60. By adjusting the ratio of content by weigh to the above-described ranges, a sufficient level of flame resistance may be ensured, the fluidity in the process of molding may be kept desirable, and the bleeding of the flame retarder may be suppressed to a sufficient degree.

These thermoplastic resins may be modified using an acid aiming at improving compatibility with the polyamide resin, typically by using an unsaturated carboxylic acid such as maleic acid or itaconic acid, acid anhydrides of these acids, or derivatives of these acids. The acid modification is not always necessarily carried out before being kneaded with the polyamide resin, but may be modified at the time of kneading with the polyamide resin, by mixing any of these modifiers.

The content of the thermoplastic resins other than the polyamide resin may be adjusted preferably to 0.5 to 5% by weight, and more preferably 0.8 to 3% by weight of the composition of the present invention (assuming the total of all components as 100% by weight). Mold deposit and bleeding of the flame retarder may be suppressed to a sufficient degree, by adjusting the content to 0.5% by weight or more, and the tracking resistance may preferably be suppressed from degrading and the productivity may preferably be improved, by adjusting the content to 5% by weight or less.

The content of the (B) phosphorus-containing flame retarder in the composition of the present invention is adjusted to 2 to 20% by weight, preferably adjusted to 2 to 15% by weight, and more preferably adjusted to 2 to 10% by weight.

The flame resistance may be improved by adjusting the content to 2% by weight or more, and the mechanical strength may be suppressed from degrading, and troubles such as failure in mold releasing and mold pollution may be avoidable, by adjusting the content to 20% by weight or less.

The composition of the present invention may be added with any of flame retarders other than the (B) phosphorus-containing flame retarder, which are exemplified by those of triazine-base, metal hydrate-base, and silicone-base, so far the object of the present invention will not be obstructed. Among these, the triazine-base flame retarder is preferable, and melamine cyanurate is more preferable.

The contents of these, and other flame retarder components are adjusted preferably to 0.5 to 10% by weight, and more preferably to 0.5 to 8% by weight of the composition of the present invention (assuming the total of all components as 100% by weight). A sufficient level of flame resistance may be expressed, by adjusting the content to 0.5% by weight or more, and the resin may preferably be suppressed from decomposing in the process of molding, by adjusting the content to 10% by weight or less. Of course, it is not always necessary to add the other flame retarders to the composition of the present invention.

The composition of the present invention may be added with a flame co-retardant, for the purpose of enhancing the flame resistance. Preferable examples of the flame retardant additive may be exemplified by magnesium hydroxide, aluminum hydroxide, zinc sulfate, iron oxide, boron oxide, and metal borate. Among these, magnesium hydroxide and metal borate are preferable, and zinc borate is particularly preferable.

In the present invention, the metal borate adoptable as the flame co-retardant is preferably such as stable under conditions generally adopted for the processing, and containing no volatile. The metal borate may be exemplified by alkali metal salts of boric acid (sodium tetraborate, potassium metaborate, etc.), and alkali earth metal salts (calcium borate, magnesium orthoborate, barium orthoborate, zinc borate, etc.). Among these, representative one is a hydrated zinc borate represented by $2ZnO.3B_2O_3.xH_2O$ (x=3.3 to 3.7), preferably the one represented by $2ZnO.3B_2O_3.3.5H_2O$, and more preferably the one stable up to 260° C. or above.

In the present invention, from the viewpoints of the mechanical strength and the appearance of the molded article, the metal borate preferably has a weight-average particle size of 30 μm or smaller, and more preferably 20 μm or smaller. By using the powder having a particle size of 1 to 20 μm, the mechanical strength may preferably be stabilized.

The content of the metal borate is preferably adjusted, for example, to 6% by weight or less of the composition of the present invention (assuming the total of all components as 100% by weight). The resin may be suppressed from decomposing in the process of molding, by adjusting the content to 6% by weight or less. From the viewpoints of balance among of flame resistance, electrical characteristics and mechanical characteristics, the content is more preferably adjusted to 1 to 6% by weight, and still more preferably to 2 to 5% by weight. Addition of the metal borate within the above-described ranges is preferable, because the content of the (B) phosphorus-containing flame retarder may be reduced, and thereby the mold releasing performance may be improved.

The (C) glass fiber having a non-circular cross-section adopted in the present invention is characterized in that the sectional geometry thereof is non-circular, rather than circular having conventionally been most popular. It has generally been known that a resin composition mixed with fibrous reinforcing filler, such as glass fiber, is elongated in the duration of combustion in the evaluation of flame resistance, as compared with resin compositions not mixed with fibrous reinforcing filler, making it difficult to achieve, for example, V-0 specified by UL94. In contrast, it was found out to our surprise that when the glass fiber has a non-circular sectional geometry as stipulated in the present invention, increase in the duration of combustion was suppressed as compared with the case where a circular cross-sectioned glass fiber was added, and the content of the flame retarder was decreased, so that a desired flame resistance could be achieved almost without sacrificing the mechanical characteristics inherent to the glass-fiber-reinforced, polyamide resin composition.

Although the reason why the sectional geometry of the glass fiber affects the duration of combustion is not clear, one possible reason may be such that the glass fiber having a non-circular cross-sectional geometry has a specific area larger than that of the circular cross-sectioned glass fiber, that is, provides a larger area of contact between the glass fiber and the polyamide resin component, so that heat is supposed to diffuse more readily and widely through the glass fiber in the process of combustion. If the content of glass fiber is large enough, more specifically to as much as 20% by weight or more, and even as much as 30% by weight or more in the composition of the present invention, a large effect of insulation of heat may be obtained, so that addition of the glass fiber having a non-circular cross-section may readily achieve V-0 specified by UL94.

The (C) glass fiber having a non-circular cross-sectional geometry used for this purpose is a glass fiber characterized by a cross-sectional geometry, taken in the direction normal to the longitudinal direction of fiber, having the outer circumferential length of 1.05 to 1.8 times, and more preferably of 1.1 to 1.6 times, longer than that of the circular cross-sectioned glass fiber having the equal sectional area. The multiplication factor of the outer circumferential length with respect to a circular section is typically given as 1.13 for square section, 1.28 for equilateral triangle section, and 1.41 for rectangular section having an aspect ratio of 4. Preferable examples of specific cross-sectional geometries are such as those illustrated in FIG. 1 of Patent Document 5 (Japanese Laid-Open Patent Publication No. 62-268612), which include a cocoon geometry narrowed at the center portion in the longitudinal direction as illustrated in FIG. 1 (i); an oblong circular geometry having parallel portions symmetrically around the center of gravity as illustrated in FIG. 1 (ro); an oval geometry as illustrated in FIG. 1 (ha); and semicircular, arch, circular arc, and rectangular geometries, wherein geometries classified into cocoon, rectangle, oblong circle and oval are preferable. The effect on reduction in the duration of combustion may be enhanced, by adjusting the multiplication factor of the outer circumferential length to 1.05 or larger, and manufacturing of the glass fiber having a non-circular cross-section may be facilitated, by adjusting the multiplication factor to 1.8 or smaller.

The sectional area of the (C) glass fiber having a non-circular cross-section is preferably $2 \times 10^{-5}$ to $8 \times 10^{-3}$ mm$^2$, more preferably $8 \times 10^{-5}$ to $8 \times 10^{-3}$ mm$^2$, and still more preferably $8 \times 10^{-5}$ to $8 \times 10^{-4}$ mm$^2$. By adjustment of the sectional area to $2 \times 10^{-5}$ mm$^2$ or larger, manufacturing of the glass fiber, and handling thereof in the process of manufacturing resin composition pellets used for molding may preferably be facilitated. In addition, by using the glass fiber having the sectional area within the above-described ranges, the area of contact with the polyamide resin may be increased, and thereby a sufficient effect of reinforcement may be obtained.

Note, that the outer circumferential length and the sectional area of the glass fiber may be obtained by observing the section of the glass fiber, used for manufacturing the resin composition, under a microscope at an appropriate magnification, measuring the actual length of 1000 to 2000 glass fibers on thus obtained image using an image analysis software, exemplified by "Image-Pro Plus" from Planetron, and by taking a number-average of the obtained values.

The length of the (C) glass fiber having a non-circular cross-section may be arbitrary, and may appropriately be selectable depending on a desired balance of the mechanical characteristics and deformation of the molded article. Shorter average fiber length of the glass fiber may be more preferable in view of reducing the amount of deformation of the molded article, meanwhile longer average fiber length may be more preferable in view of expressing high mechanical strength. The average fiber length in the molded article may appropriately be adjustable depending on required performances. Methods of adjusting the average fiber length may be exemplified by selection of the average fiber length of the glass fiber used for manufacturing of the resin composition; selection of conditions of a molding machine including screw configuration, finish of inner walls of screw and cylinder, nozzle diameter, and mold structure; adjustment of molding conditions in the process of plasticization, weighing, injection and so forth; and addition of lubricant or plasticizer to the material to be molded. The average fiber length of the glass fiber in the molded article is generally 30 to 2000 µm, preferably 50 to 1000 µm, and more preferably 100 to 600 µm. By adjusting the average fiber length to 30 µm or longer, an effect of reinforcement by the glass fiber may effectively be expressed, meanwhile by adjusting the average fiber length to 2000 µm or shorter, deformation of the molded article due to warping or shrinkage may be reduced, and thereby melt kneading with the polyamide resin and molding of reinforced polyamide resin composition may be facilitated. The glass fiber adoptable herein may be selected from those of long fiber type (roving) and short fiber type (chopped strand), for example.

Measurement of the average fiber length in the molded article may be targeted at the glass fiber which is remained typically after ashing of the resin composition in an electric oven at 600° C. for 2 to 3 hours so as to combust only the resin component. The glass fiber remained after the ashing is spread and dispersed using tweezers into an aqueous solution of a neutral detergent, while taking care to avoid fracture, the dispersed aqueous solution is transferred onto a slide glass using a pipette, observed under a microscope at a magnification of 20× and 40×, and the actual length of 1000 to 2000 glass fibers is measured on thus obtained image using an image analysis software, exemplified by "Image-Pro Plus" from Planetron. A number-average value of the obtained fiber length was defined as the average fiber length.

In addition, from the viewpoints of handlability and adhesiveness between the polyamide resin and the glass fiber, it may be preferable to treat, if necessary, the (C) glass fiber having a non-circular cross-section used in the present invention using a sizing agent and/or a surface modifier. As the sizing agent and/or surface modifier, any publicly-known sizing agents and surface modifiers such as epoxy-base compound, isocyanate-base compound, silane-base compound, and titanate-base compound may be adoptable, wherein the amount of adhesion is preferably 10% by weight or less, and more preferably 0.05 to 5% by weight, of the weight of glass fiber. Necessary and sufficient level of effect may be obtained in an economical manner, by adjusting the amount of adhesion to 10% by weight or less. The glass fiber may preliminarily be subjected to surface modification or sizing using these compounds, or may be subjected to surface modification by adding the above-described treatment agents, separately from the untreated glass fiber, in the process of manufacturing of the resin composition of the present invention.

The (C) glass fiber having a non-circular cross-section may be manufactured typically by spinning using, as a bushing used for ejecting melt glass, a nozzle having an appropriate hole geometry such as oblong circle, oval, rectangular slit or the like. Alternatively, the glass fiber may be manufactured also by spinning melt glass from a plurality of nozzles having various sectional geometries (including circular section) and provided closely adjacent from each other, and by bonding the spun melt glass yarns with each other to produce a single filament. These methods of manufacturing are disclosed typically in Japanese Laid-Open Patent Publication No. 7-291649, Japanese Laid-Open Patent Publication No. 2000-344541 and so forth.

The content of the (C) glass fiber having a non-circular cross-section in the composition of the present invention is 20 to 65% by weight, preferably 30 to 60% by weight, and more preferably 35 to 60% by weight. The duration of combustion may effectively be reduced by adjusting the content to 20% by weight or more, and molding of the polyamide resin composition may be facilitated by adjusting the content to less than 65% by weight.

In the present invention, so far the characteristics of the composition of the present invention will not be impaired, the composition may be added also with publicly-known additives, other than the above-described essential components, which include nucleating agent such as talc; stabilizers of copper halide base (for example, copper iodide, copper chloride, copper bromide) and/or alkali metal halide base (for example, potassium iodide, potassium bromide); antioxidants of hindered phenol base and phosphite base; inorganic filler other than the glass fiber having a non-circular cross-section, such as wollastonite; mold releasing agent; pigment; dye; anti-static agent; UV absorber; and impact modifier (for example, those of polyester base, polyolefin base, modified/unmodified elastomers other than those of styrene base).

In the present invention, among these additives, the nucleating agent is preferably added in view of raising the crystallization speed so as to improve the moldability. The nucleating agent may generally be exemplified by inorganic ones such as talc and boron nitride, but also organic nucleating agent may be added. The content of the nucleating agent in the composition of the present invention is preferably 0.1 to 1.0% by weight, and more preferably 0.2 to 0.5% by weight (assuming the total of all components as 100% by weight). An effect as the nucleating agent may fully be expressed by adjusting the content to 0.1% by weight or more, and the strength and impact value may be prevented from degrading due to foreign matter effect in a cost-effective manner without needing no excessive amount of addition, by adjusting the content to 1.0% by weight or less.

The composition of the present invention may preferably be added with a mold releasing agent, in view of improving the mold releasing performance in the process of molding. The mold releasing agent is preferably such as being unlikely to degrade the flame resistance of the composition of the present invention, and may be exemplified by calboxylic amide-base wax, bisamide-base wax, and metal salt of long-chain fatty acid.

The carboxylic amide-base wax may be obtained by dehydration reaction of a mixture of a higher aliphatic monocarboxylic acid and a polybasic acid, with a diamine compound.

The higher aliphatic monocarboxylic acid is preferably a saturated aliphatic monocarboxylic acid and hydroxycarboxylic acid having 16 or more carbon atoms, and may be exemplified by palmitic acid, stearic acid, behenic acid, montanic acid, and 12-hydroxystearic acid.

The polybasic acid is a carboxylic acid of two or higher degree of basicity, and may be exemplified by aliphatic dicarboxylic acids such as malonic acid, succinic acid, adipic acid, sebacic acid, pimelic acid, and azelaic acid; aromatic dicarboxylic acids such as phthalic acid, and terephthalic acid; and alicyclic dicarboxylic acids such as cyclohexane dicarboxylic acid, and cyclohexyl succinic acid.

The diamine compound may be exemplified by ethylene diamine, 1,3-diaminopropane, 1,4-diaminobutane, hexamethylene diamine, metaxylylene diamine, tolylene diamine, paraxylylene diamine, phenylene diamine, and isophorone diamine.

The carboxylic amide-base wax used in the present invention may arbitrarily be adjustable in the softening point thereof, by varying the ratio of mixing of the polybasic acid to the higher aliphatic monocarboxylic acid used for manufacturing. The ratio of mixing of the polybasic acid preferably falls in the range from 0.18 to 1 mol with respect to 2 mol of higher aliphatic monocarboxylic acid. The amount of use of the diamine compound preferably falls in the range from 1.5 to 2 mol with respect to 2 mol of higher aliphatic monocarboxylic acid, and may be variable with the amount of the polybasic acid used herein.

The bisamide-base wax may be exemplified by compounds composed of diamine compound and a fatty acid compound such as N,N'-methylenebis(stearyl amide) and N,N'-ethylenebis(stearyl amide); and dioctadecyl dibasic acid amides such as N,N'-dioctadecyl terephthal amide.

The metal salt of long-chain fatty acid is a metal salt of long-chain fatty acid having 16 to 36 carbon atoms, and may be exemplified by calcium stearate, calcium montanate, sodium montanate, zinc stearate, aluminum stearate, sodium stearate, and lithium stearate.

The content of the mold releasing agent is 0.001 to 1% by weight, and preferably 0.005 to 0.7% by weight, in the composition of the present invention (assuming the total of all components as 100% by weight). A sufficient level of mold releasing effect and improved moldability may be obtained, by adjusting the content to 0.001% by weight or more, meanwhile the dispersibility of the flame retarder in the resin composition may be improved, and the flame retardancy and electrical characteristics may be suppressed from degrading, by adjusting the content to 1% by weight or less.

Methods of mixing the (A) polyamide resin with the (B) phosphorus-containing flame retarder, the (C) glass fiber having a non-circular cross-section, and the other components to be optionally mixed, may be carried out by various publicly-known means, at an arbitrary stage up to a point of time immediately before the final molded article is molded. A most convenient method is to simply mix the polyamide resin, the phosphorus-containing flame retarder, the glass fiber, and other components to be optionally mixed, by dry blending. Alternatively, also a method of forming the dry blend into pellets by melt-mixing extrusion is convenient and preferable. In the process of melt-mixing extrusion, the polyamide resin and the flame retarder, and the other components to be optionally mixed may preferably be fed together from a hopper port of an extruder, meanwhile the glass fiber may preferably be fed from a side-feeding port, in view of proceeding a stable mixing while reducing fracture of the glass fiber. Alternatively, the composition of the present invention may be obtained also by another method, by which the phosphorus-containing flame retarder or the glass fiber excessive to a predetermined ratio of mixing is kneaded into a part of the polyamide resin so as to prepare master pellets, the master pellets are then mixed with the residual components by dry blending, followed by melt-mixing extrusion.

Methods of melt-mixing extrusion may be any publicly-known ones. The melt-mixing extrusion may be proceeded typically by using single-screw or double-screw extruder, vent-type extruder, banbury mixer and analogous apparatuses. The vent-type extruder has an effect of removing gas (air and moisture) contained in the resin composition, to thereby improve the adhesiveness between the glass fiber and the resin, and an effect of removing any components, such as oligomers, causative of non-conformities in the process of molding. In the present invention, the moisture content in the resin composition is preferably adjusted to 0.2% by weight or less, using the vent-type extruder. By adjusting the moisture content as described in the above, mold pollution caused by generation of gas in the process of molding may more readily be suppressed, and the molded article having excellent appearance may more readily be obtained.

When molded articles such as electric/electronic component including connecter and breaker, and electrical components for automobiles are manufactured using the composition of the present invention, the manufacturing may be proceeded by general procedures such that the polyamide resin composition in a form of dry blend or pellets is fed to various types of molding machines such as injection-molding machine and further into a mold, cooled, and then taken out.

The composition of the present invention does not produce a highly-corrosive hydrogen halide gas in the process of combustion, and is excellent in all of the flame resistance, mechanical characteristics and electrical characteristics, when added with the glass fiber, in particular to as much as 30% by weight or more in the composition of the present invention, so that it is suitable for various components in the electrics/electronics industry including connector, breaker and magnet switch; and for materials for electrical components in the industrial field of vehicles such as automobiles.

EXAMPLES

The present invention will further be detailed below referring to Examples, but is not limited thereto, so far as they do not depart from the gist of the present invention.

Characteristics of the individual components and method of evaluation and test of the obtained compositions in the examples below will be listed in the next.

Components Used in Examples (A) Polyamide Resin:

(A-1) Polyamide MXD6; "trade name: MX Nylon 6000" from Mitsubishi Gas Chemical Company, Inc., number-average molecular weight=16,000
(A-2) Polyamide 66; "trade name: Zytel 101" from DuPont, number-average molecular weight=20,000

(B) Flame Retarder:

(B-a) Melamine polyphosphate: "trade name: Melapur 200/70" from CIBA Specialty Chemicals Inc., weight-average particle size=5 to 10 μm, phosphorus content=approximately 13% by weight, nitrogen content=approximately 43% by weight
(B-b) Aluminum salt of 1,2-ethyl methyl phosphinate obtained by the method below: weight-average particle size=30 to 40 μm, phosphorus content=approximately 23% by weight
[Method of Manufacturing Aluminum Salt of 1,2-Ethyl Methyl Phosphinate]

Into 6.5 liters of water, 2106 g (19.5 mol) of ethyl methyl phosphinate was dissolved, 507 g (6.5 mol) of aluminum hydroxide was added under vigorous stirring, and the mixture was heated to 85° C. The mixture was stirred at 80 to 90° C. for 65 hours in total, then cooled to 60° C., and filtered under suction. The fine particle obtained after being dried in a vacuum drying cabinet at 120° C. until the weight reached constant gave a yield of 2140 g, and did not melt at 300° C. or below.
(B-c) Phenoxyphosphazene compound obtained by method of manufacturing below
[Method of Manufacturing Phenoxyphosphazene Compound]

Into 1-liter, four-necked flask provided with a stirrer, a thermometer and a reflux condenser, 123.0 g (1.30 mol) of phenol was placed, 500 ml of tetrahydrofuran was added, and the content was stirred for homogeneous dissolution. Next, 7.6 g of metal sodium was added while keeping the temperature of solution at 25° C. or below, the temperature was then elevated over 1 hour up to 62° C., to thereby prepare a sodium phenolate solution. In parallel with this reaction, 290 g of a 20% by weight chlorobenzene solution containing 58 g (0.5 unit mol) of dichlorophosphazene oligomer (a mixture of 59% by weight of trimer, 12% by weight of tetramer, 11% by weight of pentamer and hexamer, 3% by weight of heptamer, 15% by weight of octamer or larger oligomers) was placed in a 2-liter, four-necked flask, and the sodium phenolate solution prepared in the above was dropwisely added under stirring at 25° C. or below. After the dropping, the mixture was allowed to react under stirring at 71 to 73° C. for 15 hours. After completion of the reaction, the reaction mixture was condensed, re-dissolved in 500 ml of chlorobenzene, washed with water, washed three times using a 5% aqueous sodium hydroxide solution, followed by three times each of washing using a 5% sulfuric acid, washing using a 5% aqueous sodium bicarbonate solution and washing using water in this order, the solution was condensed to dryness, to thereby obtain 108 g of a pale yellow waxy product. It was confirmed that the yield of the product was 98.5%, a weight-average molecular weight based on GPC analysis of the product was 810 on the polystyrene basis, the amount of residual chlorine in the product was 0.09%, and that the product was confirmed as a compound represented by a chemical formula "N=P(OPh)$_{2.00}$" based on phosphorus and CHN element analysis. Note that -Ph represents a phenyl group.
(B-d) Brominated polystyrene; "trade name: PDBS-80" from Great Lakes Chemical Corporation Japan, Ltd.

(C) Glass Fiber:

(C-1) Non-circular-cross-sectioned glass fiber; "trade name: CSG3PA820" from Nitto Boseki Co., Ltd., a glass fiber having an elliptic section, major axis=28 μm, minor axis=7 μm, sectional area=19.5×10$^{-5}$ mm$^2$, outer circumferential length of section=70 μm, multiplication factor of the outer circumferential length with respect to a circular cross-sectioned glass fiber having the equal sectional area=1.4, (Note that the "major axis" represents the maximum straight distance in the oblong circular section, and the "minor axis" represents the minimum straight distance in the oblong circular section. These straight distances were determined by measuring the actual sizes on an image obtained by microscopic observation.), average fiber length=3 mm
(C-2) Circular cross-sectioned glass fiber; "trade name: T283" from Nippon Electric Glass Co., Ltd., average fiber diameter=13 μm, sectional area=13.3×10$^{-5}$ mm$^2$, average fiber length 3=mm Flame Co-Retardant:

Zinc borate; "trade name: Firebrake ZB" from Borax Japan, $2ZnO.3B_2O_3.3.5H_2O$, weight-average particle size=7 to 9 μm
Antimony trioxide; "trade name: PATOX-M" from Nihon Seiko Co., Ltd.

Other Components:

Modified polyphenylene ether resin (modified PPE) obtained by the method described below, SEBS content=13% by weight
[Method of Manufacturing Modified Polyphenylene Ether Resin]

One hundred parts by weight of a polyphenylene ether resin ("trade name: PX100L" from Polyxylenol Singapore Pte, Ltd., poly(2,6-dimethyl-1,4-phenylene)ether, specific viscosity measured at 30° C. in chloroform=0.3 dL/g), 0.8 parts by weight of maleic anhydride (first grade reagent), and 15 parts by weight of styrene-base resin (hydrogenated product of styrene-base compound and conjugated dien-base compound block copolymer, "trade name: Kraton G1652" from Shell, number-average molecular weight=49,000) were thoroughly mixed using a supermixer, the obtained mixture was melted and kneaded using a double-screw extruder ("TEX30XCT" from The Japan Steel Works, Ltd.), and palletized.

Mold Releasing Agents:

Carboxylic acid amide-base wax; "trade name: WH255" from Kyoeisha Chemical Co., Ltd.
Calcium montanate; "trade name: Licomont CAV102" from Clariant Japan Crystal Nucleating Agent:

Talc; "trade name: Micron White #5000A" from Hayashikasei, Inc.

<Methods of Evaluation>
[Flame Resistance]
Combustion test pieces of 5×1/2×1/16 inches in size manufactured by the method described later were tested according to UL-94.

[Mechanical Strength]
ISO test pieces were manufactured by the method described later were subjected to flexural tests (flexural strength and flexural modulus) according to ISO178, and to Charpy impact test (notched, and unnotched) according to ISO179.

[Tracking Resistance]
Test pieces of 100×100×3 mm in size manufactured by the method described later were measured according to IEC60112. The measurement was made while varying the applied voltage in 25-V steps, and the tracking resistance was evaluated at a maximum voltage not causative of dielectric breakdown.

[Mold Pollution]
Test pieces of 100×100×3 mm in size were manufactured in 100 successive shots by the method described later, and pollution on the surface of the mold after 100 shots was observed. Evaluation was made to give ⊚ for those having no adhered matter, ○ for those having almost no adhered matter (area covered with adhered matter is less than 5% of the surface area of mold), Δ for those having somewhat larger amounts of adhered matter (area covered with adhered matter is 5% or more and less than 20% of the surface area of mold), and x for those having large amounts of adhered matter (area covered with adhered matter is 20% or more of the surface area of mold).

[Gas Generated from Pellets]
Five grams of the pellets of the compositions manufactured by the method described later were weighed, and subjected to measurement using a thermal-desorption gas chromatograph (automatic thermal desorption system: "ATD400" from Parkin-Elmer, GC-MS system: "QP5050" from Shimadzu Corporation). The weighed pellets were packed in a first glass tube, helium gas was allowed to flow therethrough at a flow rate of 50 ml/s, and heated at 300° C. for 10 minutes. A second tube packed with an adsorbent TENAX was cooled to −15° C., and the generated gas was trapped. The second glass tube was then rapidly heated to desorb the adsorbed gas, the desorbed gas was introduced into GC-MS and identified. Samples having no hydrogen halide gas detected therefrom were denoted as "no", and samples having the gas detected therefrom were denoted as "yes".

Examples 1 to 14 and Comparative Examples 1 to 8

The components other than the glass fiber were mixed by dry blending according to ratios of mixing listed in Tables 1 to 3, and the mixtures were melted and kneaded using a vented double-screw kneader "TEX30HCT" (with a 12-block barrel configuration) from The Japan Steel Works, Ltd., at a cylinder temperature of 280° C., at a screw rotating speed of 200 rpm, while supplying the glass fiber by side feeding through the ninth block counted from the hopper side, and thereby the pellets of the polyamide resin composition were manufactured. The obtained resin composition pellets were dried at 80° C. for 12 hours, and molded using an injection-molding machine "ROBOSHOTα-100iA" from FANUC Ltd., at a cylinder temperature of 280° C., and a mold temperature of 120° C., to thereby manufacture the individual test pieces described in the above. The obtained test pieces were evaluated as described in the above. Results are shown in Tables 1 to 3.

TABLE 1

|  |  |  | Example 1 | Example 2 | Example 3 | Example 4 | Example 5 |
|---|---|---|---|---|---|---|---|
| A-1 | Polyamide MXD6 | wt % | 38 | 38 | 39 | 38 | 53.6 |
| A-2 | Polyamide 66 |  | 3.5 | 3.5 | 3.5 | 3.5 | 4.9 |
| B-a | Melamine polyphosphate |  |  |  |  | 2 |  |
| B-b | Aluminum ethyl methyl phosphinate |  | 7 | 7 | 7 | 5 | 10 |
| B-c | Phenoxyphosphazene compound |  |  |  |  |  |  |
| B-d | Brominated Polystyrene |  |  |  |  |  |  |
| C-1 | Non-circular-cross-sectioned glass fiber |  | 50 | 50 | 50 | 50 | 30 |
| C-2 | Circular-cross-sectioned glass fiber |  |  |  |  |  |  |
| Flame co-retardant | Zinc borate Antimony trioxide |  |  |  |  |  |  |
| Compatibilizer | Modified PPE |  | 1 | 1 |  | 1 | 1 |
| Mold releasing agent | Carboxylic amide-base wax Calcium montanate |  | 0.3 | 0.3 | 0.3 | 0.3 | 0.3 |
| Nucleating agent | Talc |  | 0.2 | 0.2 | 0.2 | 0.2 | 0.2 |
|  |  | Evaluation |  |  |  |  |  |
| Flame resistance |  | — | — | V-0 | V-0 | V-0 | V-0 |
| Flexural strength |  | MPa | 250 | 256 | 260 | 250 | 195 |
| Flexural modulus |  | GPa | 18.2 | 18.3 | 18.7 | 18.0 | 13.2 |
| Charpy impact (notched) |  | kJ/m² | 7.4 | 7.8 | 7.0 | 7.0 | 6.5 |
| Charpy impact (unnotched) |  | kJ/m² | 39 | 40 | 38 | 35 | 30 |
| Tracking resistance |  | V | 400 | 400 | 400 | 400 | 400 |
| Mold pollution |  | — | ⊚ | ⊚ | ○ | ○ | ⊚ |
| Gas generated from pellets |  | — | no | no | no | no | no |

|  |  |  | Example 6 | Example 7 | Comp. Example 1 | Example 8 | Comp. Example 2 |
|---|---|---|---|---|---|---|---|
| A-1 | Polyamide MXD6 | wt % | 29.8 | 38 | 38 | 38 | 38 |
| A-2 | Polyamide 66 |  | 2.7 | 3.5 | 3.5 | 3.5 | 3.5 |

TABLE 1-continued

| | | | | | | | |
|---|---|---|---|---|---|---|---|
| B-a | Melamine polyphosphate | | 8 | 7 | | | |
| B-b | Aluminum ethyl methyl phosphinate | | 8 | | 7 | | |
| B-c | Phenoxyphosphazene compound | | | | | 2 | 2 |
| B-d | Brominated Polystyrene | | | | | | |
| C-1 | Non-circular-cross-sectioned glass fiber | | 50 | 50 | | 50 | |
| C-2 | Circular-cross-sectioned glass fiber | | | | 50 | | 50 |
| Flame co-retardant | Zinc borate | | | | | 4 | 4 |
| | Antimony trioxide | | | | | | |
| Compatibilizer | Modified PPE | | 1 | 1 | 1 | 2 | 2 |
| Mold releasing agent | Carboxylic amide-base wax | | | | 0.3 | | |
| | Calcium montanate | | 0.3 | 0.3 | | 0.3 | 0.3 |
| Nucleating agent | Talc | | 0.2 | 0.2 | 0.2 | 0.2 | 0.2 |
| | Evaluation | | | | | | |
| Flame resistance | | — | V-0 | V-0 | V-1 | V-0 | V-1 |
| Flexural strength | | MPa | 220 | 245 | 265 | 350 | 330 |
| Flexural modulus | | GPa | 17.0 | 17.6 | 18.5 | 18.5 | 18.3 |
| Charpy impact (notched) | | kJ/m$^2$ | 5.0 | 7.5 | 6.0 | 15.2 | 13.2 |
| Charpy impact (unnotched) | | kJ/m$^2$ | 25 | 41 | 44 | 60 | 62 |
| Tracking resistance | | V | 350 | 350 | 400 | 350 | 350 |
| Mold pollution | | — | ○ | ○ | ◎ | ◎ | ◎ |
| Gas generated from pellets | | — | no | no | no | no | no |

TABLE 2

| | | | Example 9 | Example 10 | Example 11 | Example 12 | Comp. Example 3 | Example 13 | Comp. Example 4 |
|---|---|---|---|---|---|---|---|---|---|
| A-1 | Polyamide MXD6 | wt % | 41.5 | | 44 | | | 20 | 20 |
| A-2 | Polyamide 66 | | | 41.5 | | 43.5 | 41.5 | 38 | 38 |
| B-a | Melamine polyphosphate | | | | | | | 4 | 4 |
| B-b | Aluminum ethyl methyl phosphinate | | 7 | 7 | 4.5 | 5 | 7 | 5 | 5 |
| B-c | Phenoxyphosphazene compound | | | | | | | | |
| B-d | Brominated Polystyrene | | | | | | | | |
| C-1 | Non-circular-cross-sectioned glass fiber | | 50 | 50 | 50 | 50 | | 30 | |
| C-2 | Circular-cross-sectioned glass fiber | | | | | | 50 | | 30 |
| Flame co-retardant | Zinc borate | | | | | | | 2 | 2 |
| | Antimony trioxide | | | | | | | | |
| Compatibilizer | Modified PPE | | 1 | 1 | 1 | 1 | 1 | 1 | 1 |
| Mold releasing agent | Carboxylic amide-base wax | | | | | | | | |
| | Calcium montanate | | 0.3 | 0.3 | 0.3 | 0.3 | 0.3 | | |
| Nucleating agent | Talc | | 0.2 | 0.2 | 0.2 | 0.2 | 0.2 | | |
| | Evaluation | | | | | | | | |
| Flame resistance | | — | V-0 | V-0 | V-0 | V-0 | V-1 | V-0 | V-2 |
| Flexural strength | | MPa | 267 | 198 | 270 | 210 | 202 | 230 | 210 |
| Flexural modulus | | GPa | 19.2 | 15.2 | 19.0 | 17.0 | 15.5 | 12.1 | 12.0 |
| Charpy impact (notched) | | kJ/m$^2$ | 6.5 | 8.3 | 7.0 | 8.5 | 7.8 | 5.5 | 5.0 |
| Charpy impact (unnotched) | | kJ/m$^2$ | 36 | 43 | 40 | 45 | 45 | 32 | 35 |
| Tracking resistance | | V | 400 | 450 | 400 | 450 | 450 | 400 | 400 |
| Mold pollution | | — | ◎ | ◎ | ◎ | ◎ | ◎ | ◎ | ◎ |
| Gas generated from pellets | | — | no | no | no | no | no | no | no |

TABLE 3

| | | | Comp. Example 5 | Comp. Example 6 | Example 14 | Comp. Example 7 | Comp. Example 8 |
|---|---|---|---|---|---|---|---|
| A-1 | Polyamide MXD6 | wt % | 69 | 69 | 65 | 38.5 | 38.5 |
| A-2 | Polyamide 66 | | | 7 | 7 | 6 | 3.5 | 3.5 |
| B-a | Melamine polyphosphate | | | | | | |
| B-b | Aluminum ethyl methyl phosphinate | | 8 | 8 | 8 | | |

TABLE 3-continued

|  |  | Comp. Example 5 | Comp. Example 6 | Example 14 | Comp. Example 7 | Comp. Example 8 |
|---|---|---|---|---|---|---|
| B-c | Phenoxyphosphazene compound | | | | | |
| B-d | Brominated Polystyrene | | | | 5 | 5 |
| C-1 | Non-circular-cross-sectioned glass fiber | 15 | | 20 | 50 | |
| C-2 | Circular-cross-sectioned glass fiber | | 15 | | | 50 |
| Flame co-retardant | Zinc borate | | | | | |
| | Antimony trioxide | | | | 2.5 | 2.5 |
| Compatibilizer | Modified PPE | | | | | |
| Mold releasing agent | Carboxylic amide-base wax | 0.5 | 0.5 | 0.5 | | |
| | Calcium montanate | | | | 0.3 | 0.3 |
| Nucleating agent | Talc | 0.5 | 0.5 | 0.5 | 0.2 | 0.2 |
| Evaluation | | | | | | |
| Flame resistance | — | — | V-1 | V-2 | V-0 | V-0 | V-0 |
| Flexural strength | MPa | 195 | 180 | 200 | 320 | 330 |
| Flexural modulus | GPa | 9.2 | 9.0 | 10.0 | 18.3 | 18.5 |
| Charpy impact (notched) | kJ/m² | 4.8 | 4.2 | 4.5 | 11.0 | 10.0 |
| Charpy impact (unnotched) | kJ/m² | 30 | 38 | 40 | 40 | 49 |
| Tracking resistance | V | 300 | 300 | 300 | 450 | 450 |
| Mold pollution | — | X | X | ○ | ◎ | ◎ |
| Gas generated from pellets | — | no | no | no | yes | yes |

It is known from Tables 1 to 3 that the composition of the present invention are excellent in all of the flame resistance, mechanical strength, and tracking resistance, without causing mold pollution and generation of gas.

It is understood from comparison between Example 1 and Comparative Example 1, between Example 8 and Comparative Example 2, between Example 10 and Comparative Example 3, and between Example 13 and Comparative Example 4, that the flame resistance may be improved by modifying the sectional geometry of the glass fiber into non-circular one, without impairing the mechanical strength.

It is understood from comparison among Example 14, Comparative Example 5 and Comparative Example 6, that the flame resistance may be improved from V-2 only up to V-1, even when the non-circular-cross-sectioned glass fiber was adopted, if the content of which was 15% by weight, which was smaller than the range stipulated by the present invention, and that the V-0 level was not achievable. In other words, it is confirmed that the content of the glass fiber, under which the flame resistance of the V-0 level is achievable within the content stipulated by the present invention, was 20% by weight in the polyamide resin composition.

Comparative Example 7 and Comparative Example 8 using a halogen-containing flame retarder were found to be successful in obtaining sufficient levels of mechanical characteristics and flame resistance, but produced a highly-corrosive hydrogen halide gas in the process of combustion.

INDUSTRIAL APPLICABILITY

As has been described in the above, the present invention is highly valuable in terms of industrial applicability, because the advantageous effects detailed below may be expected.

More specifically, the composition of the present invention does not produce any highly-corrosive hydrogen halide gas in the process of combustion, and is excellent in all of the flame resistance, mechanical characteristics and electrical characteristics, even when a high content of glass fiber is mixed therein, so that it is suitable for various components in the electrics/electronics industry including connector and breaker components; and for electrical components in the industrial field of vehicles such as automobiles, in need of high levels of flame resistance and electrical characteristics. The resin composition of the present invention does not produce any hydrogen halide gas, and may therefore raise a large effect of environmental preservation when the components are discarded.

This application is based on Japanese Patent Application No. 2006-326530 filed in Japan, the entire content of which is incorporated hereinto by reference.

What is claimed is:

1. A flame-retardant polyamide resin composition comprising, 15 to 78% by weight of a polyamide resin (A), 2 to 20% by weight of a phosphorus-containing flame retarder (B), and 20 to 65% by weight of glass fiber having a non-circular cross-section (C).

2. The flame-retardant polyamide resin composition according to claim 1, wherein the glass fiber having a non-circular cross-section (C) has an outer circumferential length of 1.05 to 1.8 times longer than an outer circumferential length of glass fiber having a circular cross-section having equal area as the non-circular cross-section.

3. The flame-retardant polyamide resin composition according to claim 1, wherein the polyamide resin (A) is at least one species selected from xylylene diamine-base polyamide resin, polyamide 66 and polyamide 6, the xylylene diamine-base polyamide resin being obtained by polycondensation reaction of xylylene diamine and α,ω-straight-chain aliphatic dibasic acid, the xylylene diamine being composed of 55 to 100 mole % of meta-xylylene diamine and 45 to 0 mole % of para-xylylene diamine.

4. The flame-retardant polyamide resin composition according to claim 1, wherein the polyamide resin (A) is a mixture of xylylene diamine-base polyamide resin and at least one species of polyamide 66 and polyamide 6, the xylylene diamine-base polyamide resin being obtained by polycondensation reaction of xylylene diamine and α,ω-straight-chain aliphatic dibasic acid, the xylylene diamine being composed of 55 to 100 mole % of meta-xylylene diamine and 45 to 0 mole % of para-xylylene diamine.

5. The flame-retardant polyamide resin composition according to claim 1, wherein the polyamide resin (A) comprises 50% by weight or above of xylylene diamine-base polyamide resin obtained by polycondensation reaction of xylylene diamine and α,ω-straight-chain aliphatic dibasic acid, the xylylene diamine being composed of 55 to 100 mole % of meta-xylylene diamine and 45 to 0 mole % of para-xylylene diamine.

6. The flame-retardant polyamide resin composition according to claim 1, wherein the phosphorus-containing flame retarder (B) contains at least one species selected from reaction product of melamine with phosphoric acid (a), (di)phosphinate salt (b) and phosphazene compound (c).

7. The flame-retardant polyamide resin composition according to claim 1, wherein the phosphorus-containing flame retarder (B) is a phosphazene compound (c).

8. The flame-retardant polyamide resin composition according to claim 1, wherein the phosphorus-containing flame retarder (B) is a mixture of reaction product of melamine with phosphoric acid (a) and (di)phosphinate salt (b).

9. The flame-retardant polyamide resin composition according to claim 1, wherein the phosphorus-containing flame retarder (B) is a mixture of reaction product of melamine with phosphoric acid (a) and (di)phosphinate salt (b), wherein the mixture ratio of (a)/(b) is 40/60 to 60/40.

10. The flame-retardant polyamide resin composition according to claim 1, further comprising 0.5 to 12% by weight of a metal borate in the composition.

11. The flame-retardant polyamide resin composition according to claim 1, further comprising 0.5 to 5% by weight of a poly(phenylene ether)-base resin, or a mixed resin of poly(phenylene ether)-base resin and styrene-base polymer in the composition.

12. The flame-retardant polyamide resin composition according to claim 1, in which the content for the glass fiber having a non-circular cross-section (C) is 30 to 60% by weight.

13. The flame-retardant polyamide resin composition according to claim 1, wherein the glass fiber having a non-circular cross-section (C) has a cross-sectional area of $2\times10^{-5}$ to $8\times10^{-3}$ mm$^2$.

14. The flame-retardant polyamide resin composition according to claim 1, further comprising a nucleating agent.

15. The flame-retardant polyamide resin composition according to claim 1, wherein the polyamide resin (A) is at least one species selected from xylylene diamine-base polyamide resin, polyamide 66 and polyamide 6, the xylylene diamine-base polyamide resin being obtained by polycondensation reaction of xylylene diamine and α,ω-straight-chain aliphatic dibasic acid, the xylylene diamine being composed of 55 to 100 mole % of meta-xylylene diamine and 45 to 0 mole % of para-xylylene diamine; and the glass fiber having a non-circular cross-section (C) has an outer circumferential length of 1.05 to 1.8 times longer than an outer circumferential length of glass fiber having a circular cross-section having equal area as the non-circular cross-section.

16. The flame-retardant polyamide resin composition according to claim 15, wherein the phosphorus-containing flame retarder (B) is at least one species selected from reaction product of melamine with phosphoric acid (a), (di)phosphinate salt (b) and phosphazene compound (c).

17. The flame-retardant polyamide resin composition according to claim 15, further comprising 0.5 to 12% by weight of a metal borate in the composition.

18. The flame-retardant polyamide resin composition according to claim 15, further comprising 0.5 to 5% by weight of a poly(phenylene ether)-base resin, or a mixed resin of poly(phenylene ether)-base resin and styrene-base polymer in the composition.

19. The flame-retardant polyamide resin composition according to claim 15, wherein the phosphorus-containing flame retarder (B) is a mixture of reaction product of melamine with phosphoric acid (a), and (di)phosphinate salt (b), wherein the mixture ratio of (a)/(b) is 40/60 to 60/40.

20. A molded article obtained by molding a flame-retardant polyamide resin composition comprising 15 to 78% by weight of a polyamide resin (A), 2 to 20% by weight of a phosphorus-containing flame retarder (B), and 20 to 65% by weight of glass fiber having a non-circular cross-section (C).

* * * * *